US00PP24356P2

(12) United States Plant Patent
Kennedy

(10) Patent No.: US PP24,356 P2
(45) Date of Patent: Mar. 25, 2014

(54) ***PRIMULA* PLANT NAMED 'K22'**

(50) Latin Name: *Primula acaulis*
Varietal Denomination: K22

(76) Inventor: Joseph Olivier Kennedy, Ballycastle (GB)

( * ) Notice: Subject to any disclaimer, the term of this patent is extended or adjusted under 35 U.S.C. 154(b) by 99 days.

(21) Appl. No.: 13/507,561

(22) Filed: Jul. 10, 2012

(51) Int. Cl.
*A01H 5/00* (2006.01)

(52) U.S. Cl.
USPC ..... Plt./472

(58) Field of Classification Search
USPC ..... Plt./472
See application file for complete search history.

*Primary Examiner* — Susan McCormick Ewoldt
(74) *Attorney, Agent, or Firm* — Penny J. Aguirre

(57) ABSTRACT

A new cultivar of *Primula* plant, 'K22', characterized by its foliage that is a blend of dark green and bronze, its large flowers that are light yellow-orange with greyed-purple veining and golden yellow centers, its relatively vigorous growth habit, and its healthy foliage that has been observed to be disease resistant.

2 Drawing Sheets

Botanical classification: *Primula acaulis*.
Variety denomination: 'K22'.

CROSS REFERENCE TO RELATED APPLICATIONS

This application is co-pending with a U.S. Plant Patent Application filed for a plant derived from the same cross in the Inventor's breeding program that is entitled *Primula* Plant Named 'K 74' (U.S. Plant Pat. No. 22,674) and *Primula* Plant Named 'K 72' (U.S. Plant Pat. No. 22,711).

BACKGROUND OF THE INVENTION

The present invention relates to a new and distinct cultivar of *Primula* plant, botanically known as *Primula* 'K22' and will be referred to hereinafter by its cultivar name, 'K22'. The new cultivar of *Primula* is a hardy herbaceous perennial grown for landscape use.

The new cultivar was derived from a controlled breeding program conducted by the Inventor at his nursery in Ballycastle, Northern Ireland. The overall purpose of the breeding program that was established in the 1980s is to make selections of *Primula* plants with unique and improved characteristics to plants from the Garryard family of primroses, a group of *Primula* cultivars that emerged in the 1950s and had the common characteristic of having bronze colored foliage.

'K22' was selected in the Inventor's greenhouse in 2006 as a single unique plant from amongst the seedlings derived from a cross made in 2003 between two unnamed plants of *Primula acaulis* from the Inventor's breeding program as the parents.

Asexual reproduction of the new cultivar was first accomplished by in vitro propagation in 2009 under the direction of the Inventor in Ballycastle, Northern Ireland. Propagation has determined the characteristics to be stable and reproduced true to type in successive generations.

SUMMARY OF THE INVENTION

The following traits have been repeatedly observed and are determined to be the characteristics of the new cultivar. These attributes in combination distinguish 'K 72' as a unique cultivar of *Primula*.

1. 'K22' exhibits foliage that is a blend of dark green and bronze-purple.
2. 'K22' exhibits large flowers that are light yellow-orange with greyed-purple veining and golden yellow centers.
3. 'K22' exhibits a vigorous growth habit for a dark foliaged cultivar of *Primula*.
4. 'K22' exhibits healthy foliage that has been observed to be disease resistant.

In comparison to its parent plants, 'K22' is more vigorous, has better bronzing to the foliage and flowers that are larger with more distinct coloration. 'K22' can be most closely compared to the cultivars 'K 74' and 'K 72' from the same breeding program. 'K 74' is similar to 'K22' in having good vigor and large flowers, however 'K 74' differs in having slightly less bronzing to the foliage and in having white flowers. 'K 72' differs from 'K22' primarily in having red flowers. 'K22' can also be compared to the cultivar 'Garryard' (syn. 'Garryard Guinever', 'Guinever'), not patented. 'Garryard' differs from 'K22' in having foliage that is less bronze in color and in having flowers that are smaller in size and pink in color.

BRIEF DESCRIPTION OF THE DRAWINGS

The accompanying colored photographs illustrate the overall appearance and distinct characteristics of the new *Primula*. The plant in the photograph is 6 months in age as grown in a 9-cm container in an unheated greenhouse in The Netherlands.

The photograph in FIG. 1 provides a side view of 'K22' in bloom.

Figure 1:
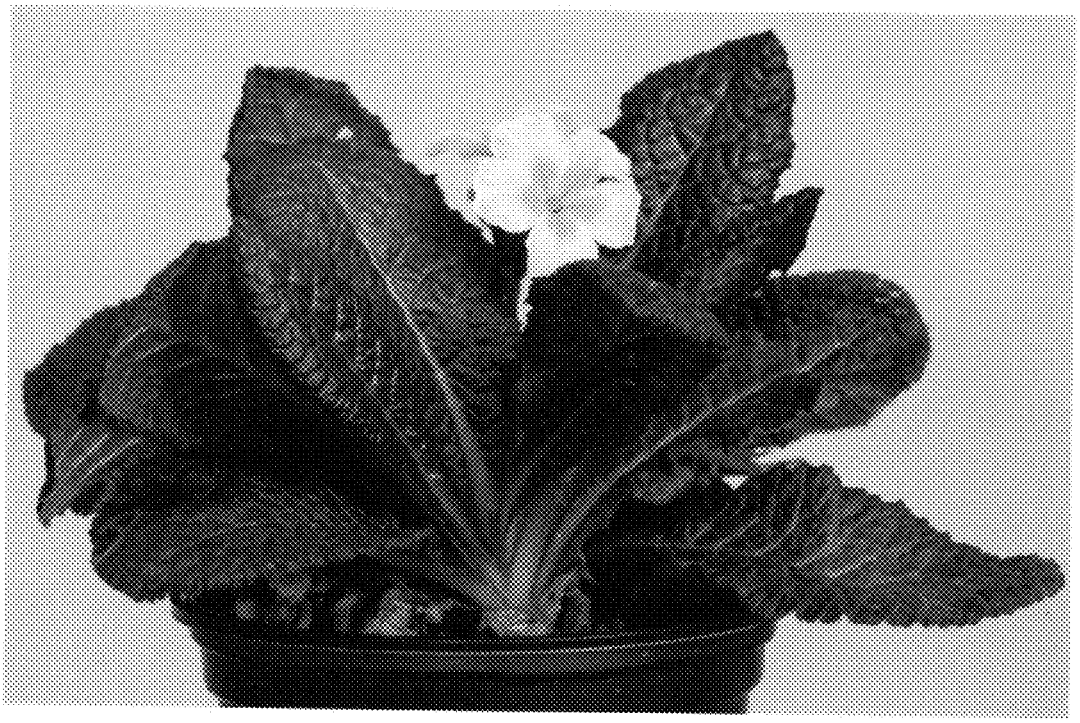
Figure 2:
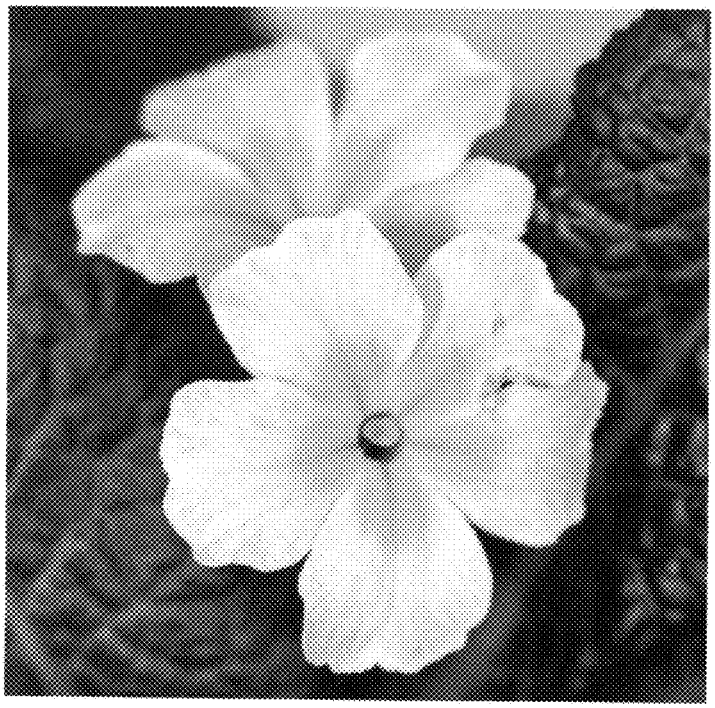

The photograph in FIG. 2 provides a close-up view of a flower of 'K22'.

Figure 3:
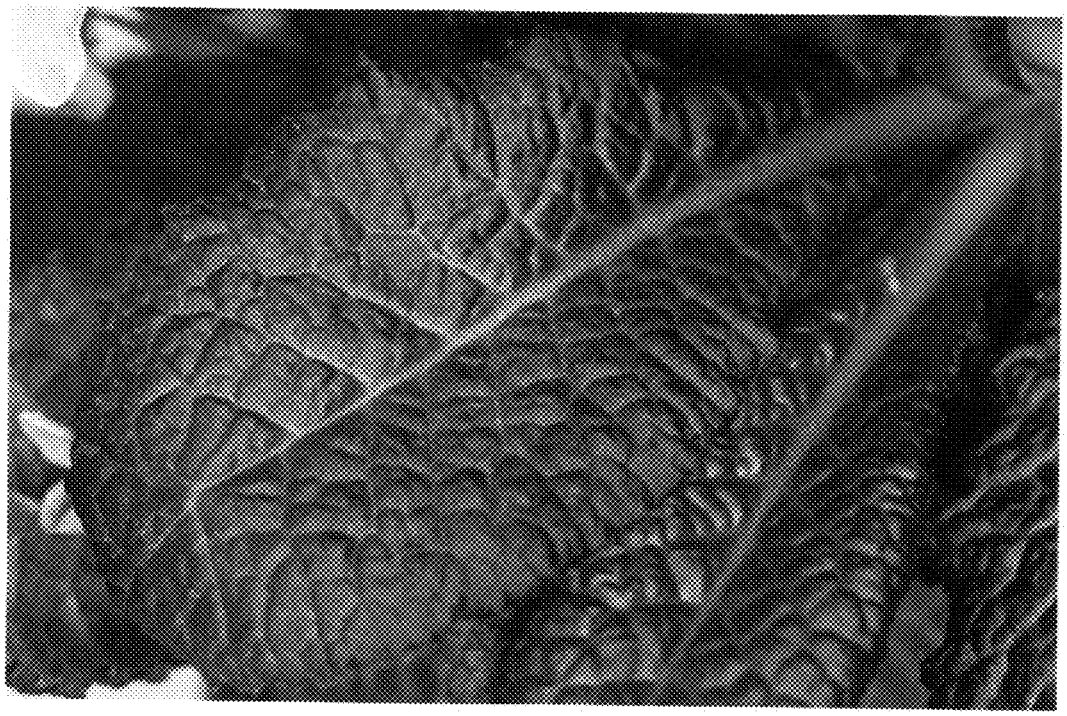

The photograph in FIG. 3 provides a close-up view of the foliage of 'K22'. The colors in the photograph may differ slightly from the color values cited in the detailed botanical description, which accurately describe the colors of the new *Primula*.

DETAILED BOTANICAL DESCRIPTION

The following is a detailed description of six month-old plants of the new cultivar as grown in 9-cm containers in an unheated greenhouse in The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Typically March to May in Ballycastle, Northern Ireland.

*Plant habit*.—Herbaceous perennial, clump-forming, tight rosette.

*Height and spread*.—Reaches about 8.5 cm in height and about 15 cm in spread.

*Hardiness*.—At least tolerant to temperatures up to 35° C. and as low as −10° C.

*Diseases*.—Has been observed to be disease free with healthy foliage.

*Root description*.—Fibrous roots.

*Branching habit*.—Basal rosettes, no lateral branches.

*Propagation*.—Tissue culture preferred.

*Growth habit*.—Vigorous for a bronzed foliaged cultivar of *Primula*.

Foliage description:

*Leaf shape*.—Obovate to oblanceolate.

*Leaf division*.—Simple.

*Leaf base*.—Broad cuneate.

*Leaf apex*.—Rounded.

*Leaf venation*.—Pinnate, on upper surface; 143B in color, strongly tinged towards the base turning 182B in color, lower surface; 147D in color, strongly tinged towards the base turning 182B in color.

*Leaf margins*.—Crenulate, finely sinuate.

*Leaf arrangement*.—Rosette.

*Leaf texture*.—Rugose to bullate and moderately glossy.

*Leaf texture*.—Upper surface smooth, lower surface moderately pubescent with thin soft hairs average length of 0.1 cm and 182C to 182D in color.

*Leaf color*.—Young upper surface; N199B, young lower surface; ranging between 148A and N199A, mature upper surface; 147A tinged with N200A especially along the margins, mature lower surface; ranging between 148A and 197A.

*Leaf size*.—About 8 cm in length and 3.6 cm in width.

*Leaf quantity*.—Average of 10 per rosette.

*Leaf attachment*.—Sessile.

Inflorescence description:

*Inflorescence type*.—Cyme.

*Inflorescence size*.—Average of 6.7 cm (including peduncle) in height and width.

*Flower number*.—Average of 10 per cyme, one cyme per rosette.

*Flower fragrance*.—Faint and sweet.

*Flower aspect*.—Upright to slightly outward.

*Flower longevity*.—About 10 days, depending on temperature and sunlight exposure.

*Flower type*.—Funnel form, lower 55% fused into a tube.

*Flower size*.—Average of 2.6 cm in diameter and 2.2 cm in depth.

*Flower buds*.—Narrow elliptic in shape, average of 2 cm in length and 6 mm in diameter, color; 183A, changing to 177B to 177C.

*Sepals*.—5, Narrow oblong, lower 62.5% fused into a campanulate shape, margin entire, average of 1.6 cm in length and 3 mm in width (measured at the base of the free part), acuminate apex, fused base, fused into a campanulate calyx with upper 37.5% free, surface is dull, main vein moderately pubescent with short soft hairs, average length of hairs 1 mm, color; N155B, color: young and mature upper surface; 147C, becoming 183B at the top, young lower surface; 187A to 187B, striped 182B to 182C, mature lower surface; 187B, striped 182C.

*Petals*.—An average of 5 per flower, rotate arrangement, spathulate, free upper 45% of the petals orbicular, lower 55% of the petals fused into a tube, surface is dull and velvety, smooth texture, margin sinuate, apex is emarginate, average of 2.6 cm in length and 1.0 cm in width, color: opening flowers upper surface; 20B to 20C, veined 174D, base ("eye") 21A, tube 13C, opening flowers lower surface; 20B to 20C, veined 184D, base 12C, tube 20C, fully opened flowers upper surface; 20B to 20C, veined 182B, base ("eye") 21A, tube 13C, fully opened flowers lower surface; 20C, veined 184B to 184C, base 12C, tube 20C, color fading to 164B, base ("eye") becomes 163A.

*Peduncle*.—Average of 0.25 cm in diameter and 2.4 cm in length, strong in strength, 182B to 182C in color, glabrous surface.

*Pedicel*.—Average of 1 mm in diameter and 2.4 cm in length, moderately strong in strength, average angle is 30° (0°=vertical), 185C in color.

Reproductive organs:

*Pistils*.—About 1 per flower, average of 1.3 cm in length, club shaped stigma 150B in color, style is an average of 1.2 cm in length and 63B in color, and ovary is 145B in color.

*Stamens*.—Average of 5, no filaments present, anthers are basifixed and oblong in shape, average of 2 mm in diameter, and 199A in color, pollen is moderate in quantity and 11A in color.

*Fruit*.—Fruit and seed production was not observed under the conditions tested.

It is claimed:

1. A new and distinct variety of *Primula* plant named 'K22' as described and illustrated herein.

* * * * *